US006796971B2

(12) United States Patent
Andersson et al.

(10) Patent No.: US 6,796,971 B2
(45) Date of Patent: Sep. 28, 2004

(54) CONTAINER FOR INTRAVENOUS ADMINISTRATION

(75) Inventors: Gunnar Andersson, Sollentuna (SE); Bert Petterson, Vallentuna (SE)

(73) Assignee: Fresenius Kabi AB (SE)

(*) Notice: Subject to any disclaimer, the term of this patent is extended or adjusted under 35 U.S.C. 154(b) by 0 days.

(21) Appl. No.: 09/812,866

(22) Filed: Mar. 21, 2001

(65) Prior Publication Data

US 2002/0128612 A1 Sep. 12, 2002

Related U.S. Application Data

(63) Continuation of application No. PCT/EP99/06976, filed on Sep. 21, 1999.
(60) Provisional application No. 60/101,604, filed on Sep. 24, 1998.

(30) Foreign Application Priority Data

Sep. 22, 1998 (SE) ........................................ 9803209-7

(51) Int. Cl.[7] ........................................ A61M 5/00
(52) U.S. Cl. ..................... 604/246; 604/247; 604/411; 604/905; 285/332
(58) Field of Search ............................ 604/246, 247, 604/249, 255, 256, 403, 411, 414, 905; 285/332

(56) References Cited

U.S. PATENT DOCUMENTS 4,210,173 A * 7/1980 Choksi et al. ........... 137/512.3
4,369,781 A * 1/1983 Gilson et al. ............... 128/214
4,493,348 A 1/1985 Lemmons ...................... 141/1
4,629,455 A * 12/1986 Kanno ........................ 604/241
4,636,204 A * 1/1987 Christopherson et al. ... 604/283
4,857,061 A * 8/1989 Miller ........................ 604/207
5,006,118 A * 4/1991 Yule .......................... 604/408
5,171,234 A * 12/1992 Jepson et al. ............... 604/283
5,242,422 A * 9/1993 Schneberger et al. ....... 604/216
5,333,761 A * 8/1994 Davis et al. ................ 222/212
5,423,791 A 6/1995 Bartlett ....................... 604/403
5,453,097 A * 9/1995 Paradis ....................... 604/247
5,474,546 A * 12/1995 Ambrisco et al. .......... 604/411
5,501,426 A * 3/1996 Atkinson et al. ........ 251/149.1
5,595,314 A * 1/1997 Weiler ......................... 215/50
5,620,427 A * 4/1997 Werschmidt et al. ....... 604/283
5,620,434 A 4/1997 Brony ......................... 604/406
5,649,637 A * 7/1997 Weiler ........................ 604/411
5,683,369 A * 11/1997 Tsukada ..................... 604/212
5,740,931 A * 4/1998 Weiler ......................... 215/50
5,782,505 A * 7/1998 Brooks et al. .............. 285/175
5,833,653 A * 11/1998 Vetter et al. .................. 604/82
5,855,230 A * 1/1999 Guala et al. .................. 138/89
5,871,110 A * 2/1999 Grimard et al. ............ 215/249
5,873,872 A * 2/1999 Thibault et al. ............ 604/414
5,944,698 A * 8/1999 Fischer et al. ............. 604/236
5,984,373 A * 11/1999 Fitoussi et al. ............... 285/92

FOREIGN PATENT DOCUMENTS

| | | | |
|---|---|---|---|
| EP | 0324257 | 7/1989 | |
| FR | 0255025 A1 * | 3/1988 | ............ A61M/5/00 |
| WO | WO 95/07720 | 3/1995 | |
| WO | WO 98/31408 | 7/1998 | |

* cited by examiner

*Primary Examiner*—Gene Mancene
*Assistant Examiner*—Frederick C. Nicolas
(74) *Attorney, Agent, or Firm*—Gilberto M. Villacorta; Katten Muchin Zavis Rosenman; Robert W. Hahl

(57) ABSTRACT

A device for storing and administering a medical fluid comprising a sealed flexible formed container with an opening part in its front end in which an insert is positioned. Over the insert, the container extends into a removable sealing cap. After removal of the sealing cap an injection means is attached to the insert and fluid administration through the insert is admitted in one direction by squeezing the container.

6 Claims, 1 Drawing Sheet

CONTAINER FOR INTRAVENOUS ADMINISTRATION

RELATED APPLICATIONS

Figure 1A:
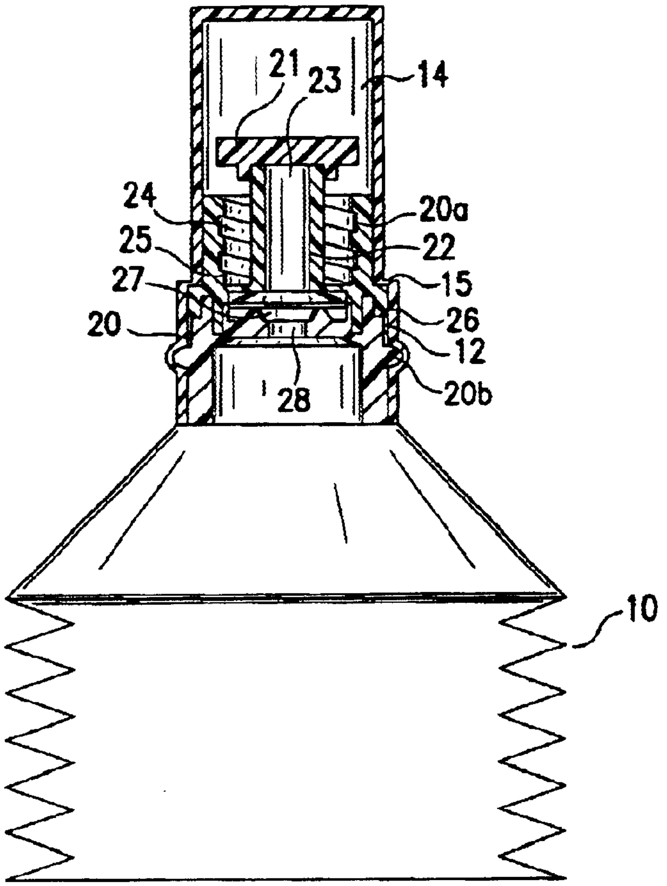

This Application is a Continuation of International Application No. PCT/EP99/06976, filed Sep. 21, 1999, which claims priority to Swedish Application No. 9803209-7, filed Sep. 22, 1998, and U.S. Provisional Application No. 60/101, 604, filed Sep. 24, 1998, each of which is herein incorporated by reference.

FIELD OF INVENTION

The present invention relates to a device for storing and administering a medical fluid, comprising a sealed flexible generally bottle formed container provided with an insert in its opening to which an injection means can be attached.

BACKGROUND OF THE INVENTION

It is a well established technique in pharmaceutical industry to manufacture prefilled bottle formed containers for sterile fluids from blow molding a polymer material, filling and sealing the so formed container in a continuous operation. Such a blow-fill-seal method is disclosed for example in U.S. Pat. No. 4,342,184. In the European patent specification EP 0 670 709, it is disclosed a container made from such a method comprising essentially only a polyolefin based material so a highly environmental friendly container is obtained with a high compatibility to the stored fluids which also satisfies the requirement that the finally sealed container shall be sterilized with high pressure steam (i.e. autoclavation at about 120° C. for more than about 15 minutes). This bottled formed container is suitable for repeated collection of fluid with a syringe needle piercing its elastomer containing resilient sealing insert. This type of containers has many advantages from their cheap and efficient production method and they will successfully replace glass bottles or ampoules in numerous applications. A drawback with these containers is that it requires a certain skill and accuracy to correctly pierce the insert to establish fluid communication between the bottle and syringe so as to collect a desired amount of stored fluid for adminstration to a patient or for transfer to another container.

EP 0 088 056 and EP 0 326 391 disclose plastic bottle formed ampoules having twist off heads and neck parts formed as a female luer so as to fit with the male luer heads of a connected syringe when transferring fluids from the bottle to the syringe. In many applications, it would be of advantage to be able to directly use the bottle formed container filled for administering its sterile fluid to a patient. The transferring step using an attachable syringe results in an extra routine and thereby a risk for contamination and faulty handling.

FR 27 18 017 discloses a bottle for liquid pharmaceuticals made of a polymeric material which is sealed with a detachable cap. The bottle has top part formed as a male luer like connection to a cannula (or a similar device) with corresponding form. After tearing off the cap 6 a lock ring 11 is engaged over the flange 10 bottle opening. The lock ring will serve as safe and tight connecting piece between the bottle opening and the cannula. The European patent application 0 788 804 describes a flexible bottle of a polymeric material. The bottle may contain a rinse fluid (sodium chloride solution) which for example can be used for flushing a catheter connected to a vein of a patient, just before the infusion of a drug or a parenteral nutrient. It generally comprises a bottle with a cap which the user removes to free its opening. A separate connecting piece with attachment means for a cannula is inserted into the opening. The assembled device is thereby ready to be used for administering the contents of the bottle to a patient, or for transferring of the fluid into another container. The device of EP 0 788 804 suffers from a number of obvious drawbacks. At first, the inserting procedure of the connector is inconvenient and results in additional handling for the hospital personal and will always include a risk for inadvertent contamination of the fluid. Secondly, the device, if used for vein flushing, may deliver air bubbles with the fluid when the fluid is administered by squeezing the flexible bottle. The introduction of air bubbles into the blood system can not be tolerated due to the risk of embolism Also U.S. Pat. No. 4,259,095, EP 0 310 227 and FR 954 795 disclose plastic bottles filled medical liquids which have removable cap parts exposing a male luer neck part for connection to a corresponding female part of a cannula. These containers aim to provide containers which directly can be transformed to an adminstration tool for injection of the stored liquid to a patient. However, as injection devices these containers in many aspects are inferior when compared to ordinary syringes operating by actuating a piston rod connected to a piston during the administration of the fluid. One drawback with conventional blow-fill-seal formed containers of this type is that the joints from the molding process when connecting the container pieces remain and cause impairments of the fitting of luer connection between the container top and a cannula. It is of further importance that they do not admit any safe routines when it comes to removing air bubbles from the injection fluids, as being performed by a routine de-aeration step with conventional syringes in order to avoid injection of air. U.S. Pat. No. 5,538,306 reveals a construction of such a bottle formed squeezable containers attachable to a cannula which aims to overcome the problems, but is complicated in construction and requires a prescribed handling including several steps. WO/95/07720 discloses a needless valve for use in intravenous infusion which is normally closed to prevent fluid communication. A needless connector can be engaged with a male element of the valve to open the valve. The administration can not be performed by simply squeezing the container. WO98/3 1408 describes a slotted-disc check valve adapted to receive flow-fittings, such as a tubing and Luer fittings. Depending on the flow direction, the check-valve opens and closes, respectively. Using an external member, the check-valve allows fluid to flow in both directions.

There is obviously a demand for bottle formed plastic containers for storing medical fluids that readily can be converted into a safe and convenient injection device with a minimum of complicated operations and thereby having the highest possible safety in terms of contamination of the fluid during the handling. This is attained by the present invention as will be explained in the following.

DESCRIPTION OF THE INVENTION

The present invention relates to a device for storing and administering a medical fluid, comprising a sealed flexible container which is generally bottle formed or of a similar shape. In its front end, the container is provided with an opening part, in which an insert is sealingly positioned. In order to protect the insert during handling and storing prior to the use of the device, the container is formed during its manufacturing so it directly extends into sealing cap over said insert. The cap is removable by being provided with weak line or a similarly rupturable zone so the user by a simple twisting motion may remove the entire cap or a substantial part thereof to expose the insert when the fluid in the container shall be used and fluid communication shall be established between the container and an attachable injection means, preferably with a conventionally shaped cannula comprising a front needle part connected to generally conical hollow rear part. This is accomplished by that the rear part of the cannula is attached to a generally tubular part of the insert with a generally conical shape in cross-section fitting with the hollow part of the cannula. Preferably, the tubular part of the insert and the hollow part of the cannula are cooperating luer fittings, so said tubular part corresponds to male luer fitting and said hollow part corresponds to a female luer fitting. Furthermore, to ensure that the injection means is safely attached, the insert is provided with a engagement means which comprises a radially extended annular recess in the insert which extends axially into the insert a sufficient distance to secure the attachment of a conventional cannula having a rear end shaped as a female luer fitting. To improve on the engagement, the outer periphery of the annular recess preferably is provided with screw threaded grooves, so as to form a luer lock attachment between the cannula and the insert of the device.

It is an important feature of the device is that it only admits fluid flow in one direction when handling and administering the medical fluid. An accidental entrance of air into the container will be avoided and thereby an accidental administration of air bubbles which at worst case may cause embolism. Therefore, the insert is provided with means so that it only admits fluid communication in one direction. Furthermore, the insert is capable of be sealed if fluid passes from the injection device through the insert into the container. This is preferably accomplished by that inserted is provided with a membrane in its fluid channel which is displaceable between a first sealing position to a second open position if a pressure is exerted on the flexible container. Preferably the membrane is axially displaceable between two predetermined positions in order to act as a check valve mechanism. The skilled person can readily select a suitable valve mechanism which does not have to be limited to the mentioned membrane and find suitable opening pressures. Suitable opening pressures for valves in the present invention are less than about 2.5 mm $H_2O$ and preferably less than about 1 mm $H_2O$. In order to provide a device which is safe for flushing and rinsing an intravenously connected catheter with sterile saline, for example of a patient confined to parenteral nutrition, it is preferred that the membrane is displaced to a sealing position by the blood pressure of the patient, so that blood not inadvertently will be sucked out into the device. It is suitable that the opening pressure of the valve mechanism must be larger than the blood pressure of the patient.

In certain applications, the bottle formed container of the device can be bellows formed to facilitate the squeezing motion required during the adminstration of its contents. The bottle formed container can also be provided with means indicating the levels of fluid and the size of required doses to be administered.

The inventive device can be manufactured with a conventional blow-fill-seal method as is more closely in the aforementioned patent specifications EP 0 670 709 and U.S. Pat. No. 4,342,184. Such method includes blow molding of a polymeric material into bottle formed shape which is filled with medical fluid, whereupon the insert is placed in the opening of the container which is finally sealed by forming a removable cap over the insert from the polymeric material. The finally assembled device can be subjected to a sterilization step by high pressure steam (autoclavation) or by means of irradiation before leaving the manufacturing plant.

The inventive device will find use in a large number of applications besides flushing of infusion means with sodium chloride solution. For example, it will be useful for supplementation of a complementary fluid to an infusion bag by piercing one of its ports, just prior to adminstration of the contents of the bag. It will also be conceivable to use the device as a single or plural dose syringe for direct administration to a patient by injection of for example antithrombotic agents such as heparin or low-molecular weight heparins like Fragmin®.

DETAILED DESCRIPTION OF THE INVENTION

Figure 1B:
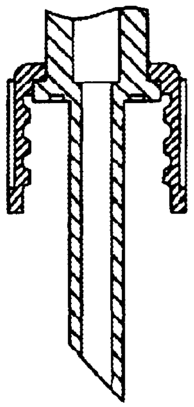

FIG. 1 shows a schematic view of the container with an axial split view of the insert.

By referring to FIG. 1, the device comprises a generally bottle formed container body 10 with opening part 12 in its front end where an insert 20 is positioned. The container extends directly into a sealing cap 14 which is made easily removable by a twisting motion of the user. For this reason the cap is provided with a preformed break line 15 which is easily rupturable. The insert has a generally tubular part 22 which can be in fluid connection with the container body. The front end of the tubular part is sealed with a plug 21 which is intended to be removed at the same time the cap is ruptured. The tubular part has a generally conical shape in cross-section so as to fit a correspondingly shaped rear hollow part of a cannula. The cannula can thereby be attached to the tubular part with a luer fitting. To assist in the attachment, the insert is provided with an annular recess 24 which extends a suitable axial distance in the insert. The recess can be provided with screw-threaded grooves 25 to improve on the engagement with the cannula. The dimension of these parts are selected so that they comply with the ISO/DIN standards for male and female luer fittings. To accomplish fluid communication only in one direction through the insert is provided with a valve mechanism. The insert comprises two parts, a front part 20A with the aforementioned tubular part and the annular recess capable establishing a luer lock connection to a cannula and rear part 20B. The parts of the insert are preferably both made of the same compatible polymer material and tightly welded together with conventional means. The rear part of the insert is provided with a sealing membrane 26 accommodated in a housing 27 which is in fluid connection with the channel 23 going through the tubular part 22 and the channel 28. The membrane is an elastic sealing silicon membrane attached in its housing 27, wherein it is axially displaceable between an open position and a sealed position. The membrane and the housing is dimensioned so that it admits fluid communication with the channel 23 when a predetermined positive pressure is exerted on the container 10, for example by squeezing it, otherwise the mechanism remains in its sealing position. The rear part of the insert will thereby act as a check valve and is capable to close and seal the device if the attached cannula is in intravenous contact with a patient and the blood pressure is exerted on the valve mechanism until a pressure exceeding the blood pressure is exerted on the container when administering medical fluid to the patient. The accordingly designed insert will provide a device which is useful both as a flushing and rinsing means for intravenous administration provisionally connected to vein of a patient and for conventional adminstration by injection of dose of a medical fluid without risking to accidentally administer air into patient that, for example, may sucked into the device by inadvertent handling. The handling of the container will be extremely simple and reliable and is initially restricted to the measures of removing the cap along the preformed break line and attaching the cannula to the insert The container can then, if necessary, subjected to a de-aeration step by gently squeezing it in an upright position until fluid expels from the needle and/or no visible signs of air bubbles remain. The administration can thereafter be performed by simply squeezing the container in a prescribed manner.

The device is preferably made substantially from polymer materials which is possible to recycle together without unnecessary labor to dismantle it and separately collect its parts. A preferred material for the container is polyolefins, especially polypropylenes and copolymers thereof. The insert can be made of polypropylenes or polycarbonates. The minor contribution of the latex membrane from the valve will not interfere with normal recycling applications, since its weight represents less than 1% of the entire container.

What is claimed is:

1. A container for storing and administering a medical fluid, comprising a sealed flexible container having at its front end an opening part in which is positioned an insert comprising a non-return valve means and a connection means, the insert being covered by a first removable sealing cap such that after removing the first sealing cap, the insert can be connected to an injection means via an annular recess provided with cooperating screw-treaded grooves, wherein the first removable sealing cap is a direct extension of said container, the connection means being covered by a second removable cap that does not cooperate with the screw-threaded grooves, and wherein the non-return valve means is arranged, when administering the fluid, so as to allow fluid communication only from the container to the injection means, if pressure is exerted on the flexible container.

2. The container according to claim 1, which can be connected to injection means comprising a cannula.

3. The container according to claim 2, wherein the connection between the insert and the injection means comprises cooperating luer fittings.

4. The container according to claim 1, wherein the non-return valve means comprises a radially extending membrane which is axially displaced from a first sealing position to a second open position if pressure is exerted on the flexible container, so as to permit fluid communication from the container to the injection means.

5. The container according to claim 4, wherein the membrane is displaced to a sealing position if actuated only by blood pressure.

6. The container according to claim 1, wherein the flexible container is shaped like a bellows.

* * * * *